United States Patent [19]

Hammond et al.

[11] Patent Number: 4,596,828
[45] Date of Patent: Jun. 24, 1986

[54] [(2-HYDROXY-5-ALKOXYPHENYL)METHYLTHIO]PHENYLMETHANOL AND DERIVATIVES THEREOF USEFUL AS ANTI-INFLAMMATORY AGENTS

[75] Inventors: Milton L. Hammond, Somerville; Robert A. Zambias, Springfield, both of N.J.

[73] Assignee: Merck & Co., Inc., Rahway, N.J.

[21] Appl. No.: 717,736

[22] Filed: Mar. 28, 1985

[51] Int. Cl.[4] ............... A61K 31/10; C07C 149/36
[52] U.S. Cl. ............... 514/712; 514/546; 514/548; 514/550; 514/713; 560/138; 560/227; 560/228; 560/255; 568/47; 568/49
[58] Field of Search ............... 568/47, 49; 560/138, 560/227, 228, 255; 514/546, 548, 550, 712, 713

[56] References Cited

U.S. PATENT DOCUMENTS

| | | | |
|---|---|---|---|
| 3,491,102 | 1/1970 | O'Shea et al. | 568/47 |
| 3,491,155 | 1/1970 | O'Shea | 568/47 |
| 3,903,257 | 9/1975 | Arai et al. | 514/712 |
| 4,358,616 | 11/1982 | Wedemeyer et al. | 568/45 |

OTHER PUBLICATIONS

Nasirov, M. N., Chem. Abstracts 93: 83546b Citing (Inst. Khim Prisadok. Baku) Sint. Issled. Biol., Soedin, Tezisy Dokl. Konf. Molodykh Uch. 6th 1978, 107–108 (Russian).
Derwent Abstract of USSR 551,326 published May 23, 1977.
Derwent Abstract of USSR 556,599 published Nov. 17, 1977.

*Primary Examiner*—Donald G. Daus
*Assistant Examiner*—Mary E. Ceperley
*Attorney, Agent, or Firm*—Theresa Y. Cheng; Michael C. Sudol

[57] ABSTRACT

[(2-Hydroxy-5-alkoxyphenyl)methylthio]phenylmethanol and derivatives thereof were prepared from an appropriate 2-hydroxy-5-alkoxybenzaldehyde with a hydroxymethylthiophenol. These compounds were found to be potent anti-inflammatory agents.

9 Claims, No Drawings

[(2-HYDROXY-5-ALKOXYPHENYL)METHYLTHIO]PHENYLMETHANOL AND DERIVATIVES THEREOF USEFUL AS ANTI-INFLAMMATORY AGENTS

BACKGROUND OF THE INVENTION

The present invention relates to novel [(2-hydroxy-5-alkoxyphenyl)methylthio]phenylmethanol and its derivatives useful as anti-inflammatory agents.

It has been observed that the novel compounds of this invention are active in vitro in both the peritoneal macrophage assay and the polymorphonuclear leukocyte assay for general anti-inflammatory activity. Specifically, they are found to be active in vivo in the mouse ear assay for topical anti-inflammatory agents. Furthermore, these compounds tend to be inactivated in vivo after deeper and longer penetration into the body system and are therefore devoid of any significant adverse side effects normally associated with systemic activity.

Recent studies demonstrated that macrophages participate in the development and progression of chronic inflammatory diseases such as rheumatoid arthritis. During the progression of inflammatory conditions, there is generally an appearance and/or presence of macrophages and lymphocytes, especially macrophages and polymorphonuclear leukocytes. Macrophages are known to secrete various products in response to inflammatory stimuli. For example:

(1) Neutral proteases—the destructive peptide bond cleaving enzymes which have been shown to be directly involved in rheumatoid cartilage destruction; and
(2) Prostaglandins (PG) (e.g., $E_2$ and $I_2$ by mouse peritoneal macrophages) and other arachidonic acid derivatives derived from both the cyclooxygenase and the lipoxygenase pathways.

These arachidonic acid oxygenation products have been identified as the critical mediators of various acute inflammatory conditions.

Accordingly, pharmacological agents which are capable of inhibiting the formation or the release of a mediator and thereby interfere with the function of macrophages or polymorphonuclear leukocytes may also be effective anti-inflammatory agents. For example, nonsteroidal anti-inflammatory drugs such as indomethacin and clinoril are known cyclooxygenase inhibitors. Through their ability to inhibit the formation of prostaglandins, they have been used for rheumatoid arthritis and osteoarthritis. Other inflammatory diseases such as emphysema, bronchial inflammation, acute respiratory distress syndrome, spondylitis, lupus, gout, and psoriasis may also be treated with these pharmacological agents.

Regarding the topical mouse ear assay, it has been previously established that classical nonsteroidal anti-inflammatory agents such as indomethacin and steroidal anti-inflammatory agents such as dexamethasone are active in this assay.

Another object of this invention is to provide appropriate processes for the preparation of the subject novel compounds.

Still a further object of the present invention is to provide a pharmaceutically acceptable composition containing an effective amount of the active compound for the treatment of various inflammatory conditions.

Finally, it is the ultimate object of this invention to develop a method of treating inflammation via the administration of a therapeutically effective amount of the novel compounds or pharmaceutically acceptable composition thereof to a mammalian species in need of such treatment.

DETAILED DESCRIPTION OF THE INVENTION

A. Scope of the Invention

This invention relates to novel compounds of formula (I):

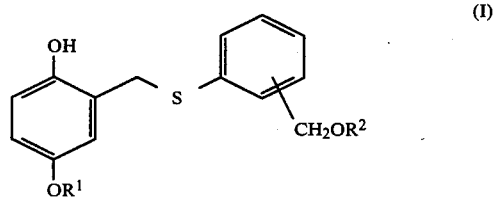

or a pharmaceutically acceptable salt thereof, wherein $R^1$ and $R^2$ independently are:

(a) hydrogen;
(b) loweralkyl especially $C_{1-6}$ alkyl such as methyl, ethyl, propyl, t-butyl, pentyl, benzyl, cyclopropyl, cyclopentyl or cyclohexyl;
(c) loweralkenyl especially $C_{2-6}$ alkenyl, for example, vinyl, allyl, and buten-2-yl;
(d) lower alkanoyl especially $C_{1-6}$ alkanoyl such as formyl, acetyl or i-propanoyl;
(e) haloloweralkyl especially $C_{1-6}$ haloalkyl such as trifluoromethyl;
(f) hydroxyloweralkyl especially hydroxy $C_{1-3}$alkyl such as $-CH_2OH$; or
(g) halo loweralkanoyl especially halo$C_{1-6}$ alkanoyl eq. $CF_3CO$.

In a preferred embodiment of this invention, the compounds are of formula (I) wherein $R^1$ and $R^2$ independently are H, or $C_{1-6}$ alkyl In a more preferred embodiment of the present invention, the compounds are of the following formula (I) wherein $R^1$ is methyl and $R^2$ is H.

B. Preparation of the Compounds within the Scope of the Invention

The novel compounds of the present invention are prepared from the following processes:

Scheme (a) for example:

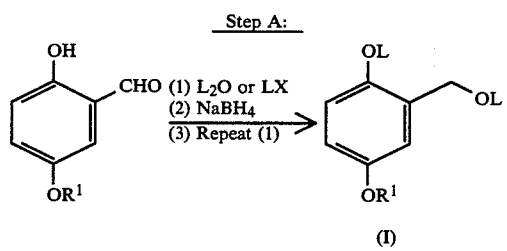

L=a good leaving group such as tosyl, acetyl or mesyl etc.
X=halo

Step B:

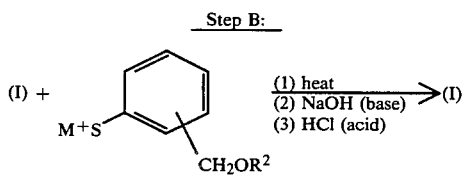

wherein M is an alkali or alkaline earth metal such as sodium, potassium or lithium.

C. Utility of the Subject Compounds of the Invention

This invention also relates to a method of treating inflammation in patients in need of such treatment. Generally, a sufficient amount of a compound of formulae (I) or a pharmaceutical composition thereof, particularly an especially preferred compound, is administered to the patient as the active constituent.

For treatment of inflammation, fever or pain, the compounds of the invention are administered topically, by inhalation spray or rectally in dosage unit formulations containing conventional non-toxic pharmaceutically acceptable carriers, adjuvants and vehicles.

The pharmaceutical compositions containing the active ingredient may be in a form suitable for topical use, for example, aqueous or oily solutions or suspensions, dispersible powders or granules, tinctures, topical aerosol emulsions, creams, ointments, jellies, suppositories or the like. Compositions intended for topical use may be prepared according to any method known to the art for the manufacture of pharmaceutical compositions and such compositions may contain one or more active compounds.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alignate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules are suitable for the preparation of an aqueous suspension by mixing them with water. They provide the active ingredient in admixture with a dispersing or wetting agent, a suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth, naturally-occurring phosphatides, for example, soy bean, lecithin, and esters or partial esters derived from fatty acids and hexitol anhydrides, for example, sorbitan mono-oleate, and condensation products of the said partial esters with ethylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sebacate, ethyl carproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.2 mg to 140 mg per kilogram of body weight per day are useful in the treatment of the above-indicated conditions (10 mg to 7 gms per patient per day). For example, inflammation is effectively treated by the administration from about 0.5 to 50 mg of the compound per kilogram of body weight per day (25 mg to 5 gms per patient per day).

The amount of active ingredient that may be combined with the carrier materials to produce a single dosage form will vary depending upon the host treated and the particular mode of administration. Dosage unit forms will generally contain between from about 25 mg to about 1 g of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Set forth below are some illustrative topical formulations containing a selected active compound of the instant invention.

Formulation Number 1—Solution (a) Distilled water qs to 100%

Procedure: Dissolve a compound of formula (I) in enough water to make 100%. Filter the solution. Apply to the affected area.

Formulation Number 2—Tincture (b) Alcohol U.S.P.—50%
Water qs to 100%

Procedure: Dissolve a compound of formula (I) in the alcohol. Add sufficient water to make 100%. Filter and apply to affected area.

Formulation Number 3—Topical Aerosol (c) Alcohol U.S.P.—5%
Isopropylmyristate—5%
Conventional halogenated hydrocarbon propellant qs 100% e.g., Freon 11 (trichlorofluoromethane), Freon 12 (dichlorodifluoromethane), Freon 14 (carbon tetrafluoride), Freon C 318 (Octafluorocyclobutane), Freon 114 (Cryofluorane), etc.

Procedure: Dissolve a compound of formula (I) in the alcohol and isopropylmyristate. Add sufficient halogenated propellant and introduce into conventional aerosol containers either by pressure or by cold filing. Apply to affected area.

Formulation Number 4—Ointment

Petrolatum U.S.P. qs to 100%

Procedure: Heat the petrolatum to 60° C. Add a compound of formula (I) and stir until thoroughly dispersed. Cool to room temperature. Apply to affected area.

D. Biological data supporting the utility of the compounds of formula (I)

The topical mouse ear assay (TME) was used to evaluate the novel compounds of the present invention for its effect on inflammatory responses elicited by topically applied phorbol myristate acetate (PMA) or topically applied archidonic acid (AA). The inflammatory responses may be in the form of edema (measured by wet weight); vascular permeability (measured by $^{125}I$-BSA accumulation); or PMN infiltration (measured by myeloperoxidase activity). A protocol of the assay and some results derived therefrom are summarized below.

Topical Mouse Ear Assay

Method: The right ears of mice (5 mice per group) were treated topically with either 5 μl PMA or 1000 μg AA alone or with the test compound in 25 μl of vehicle. The vehicle was water/pyridine/acetone (1:2:97). A control group of mice received the vehicle only. The mice were allowed food and water ad libitum during the treatment period; 2 hours for AA and 4 hours for PMA. The mice were sacrificed by cervical dislocation and a 6 mm diameter disc of tissue punched from both the treated and untreated ears. The tissue biopsies were immediately weighed and the weight increase of the treated ear relative to the weight of the untreated ear determined.

All of the data are expressed as the mean ±SEM, N=5 mice/group.

Results: The effect of 2-[2-(hydroxymethyl-phenylthiomethyl)]-4-methoxyphenol (Compound A)

| Compound | Dosage (μg) | Edema (% inhibition) |
| --- | --- | --- |
| A | 300 | 63 |
|   | 200 | 55 |
|   | 50 | 16 |
|   | 30 | 12 |
| Indomethacin | 150 | 51 |

-continued

| Compound | Dosage (μg) | Edema (% inhibition) |
| --- | --- | --- |
| Dexamethasone | 5 | 60 |

EXAMPLE 1

2-Hydroxy-5-methoxybenzyl alcohol

To a suspension of sodium borohydride (2.50 g, 65.8 mmol) in ethanol (100 mL) at 5° C. was added a solution of 2-hydroxy-5-methoxybenzaldehyde (10.00 g, 65.8 mmol) in ethanol (35 mL) dropwise. Upon completion of the addition the reaction mixture was allowed to stir for ten minutes then quenched by the dropwise addition of 10% aqueous acetic acid (75 mL). The ethanol was removed by concentration in vacuo and the resulting mixture poured into water (250 mL) and extracted with ethylacetate (3×100 mL). The combined extracts were washed sequentially with saturated sodium bicarbonate (50 mL), and brine (3×100 mL). The organic extract was dried (Na$_2$SO$_4$) and concentrated to afford a crude product (8.75 g). Trituration with hexane:ether (3:2, 25 mL) afforded 2-hydroxy-5-methoxybenzyl alcohol (7.00 g, 70%) as a white solid.

EXAMPLE 2

2-Acetoxy-5-methoxybenzyl acetate

To a solution of 2-hydroxy-5-methoxybenzyl alcohol (3.00 g, 19.5 mmol) in pyridine (30 mL) was added acetic anhydride (5.5 mL) over about one minute. The resulting mixture was heated at 80° C. for thirty minutes, allowed to cool, and poured into water 175 mL). The resulting mixture was extracted with ethyl acetate (2×75 mL) and the combined organic layer washed sequentially with 2N hydrochloric acid (2×60 mL), and brine (3×60 mL). The organic layer was dried (Na$_2$SO$_4$), filtered, and the filtrate concentrated to afford 2-acetoxy-5-methoxybenzylacetate as a pale yellow oil (4.28 g, 89%).

EXAMPLE 3

2-[2-(Hydroxymethyl)phenylthiomethyl]-4-methoxyphenol

To a solution of o-mercaptobenzyl alcohol (12.5 g, 89.3 mmol, freshly purified by HPLC) in dry dimethylformamide (95 mL) under nitrogen atmosphere was added sodium hydride (60% dispersion in mineral oil, 3.56 g) in portions. After hydrogen evolution had ceased the mixture was allowed to stir for 1.5 hours at ambient temperature then added dropwise to a solution of 2-acetoxy-5-methoxybenzyl acetate (27.0 g), 89.3 mmol) in dry dimethylformamide (250 mL). The resulting mixture was allowed to stir at room temperature for three hours then heated to 50° C. for thirty minutes. After cooling to room temperature 1.25N sodium hydroxide (250 mL) was added and the mixture stirred for one hour. The mixture was diluted with water (1200 mL) and the aqueous mixture extracted with a small portion of ether. The aqueous layer was acidified with 2.5N hydrochloric acid and extracted with ether (3×300 mL). The combined organic extracts were dried (Na$_2$SO$_4$), filtered, and the filtrate concentrated to afford the crude product as a thick oil which slowly solidified. Preparative HPLC (2:1 hexane:ethyl acetate as eluant) afforded 2-[2-(hydroxymethyl)phenylthiomethyl]-4-methoxyphenol (11.6 g, 47%). Recrystallization from hexane/methylene chloride afforded an analytical sample. m.p. 80°–82° C. Anal. C, H, S

| Element | Calculated | Found |
|---|---|---|
| C | 65.39 | 65.19 |
| H | 5.81 | 5.83 |
| S | 11.49 | 11.60 |

What is claimed is:

1. A compound of formula (I):

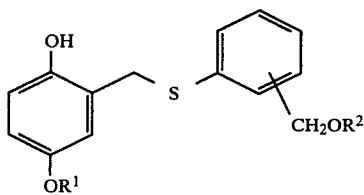

or a pharmaceutically acceptable salt thereof wherein $R^1$ and $R^2$ independently are (a) hydrogen;
(b) $C_{1-6}$alkyl;
(c) $C_{1-6}$alkenyl;
(d $C_{1-6}$ alkanoyl;
(e) halo$C_{1-6}$alkyl;
(f) hydroxy$C_{1-6}$alkyl; or
(g) halo $C_{1-6}$alkanoyl;
(h) $C_{1-6}$cycloalkyl; and
(i) benzyl.

2. The compound of formula (I) according to claim 1 wherein: $R^1$ and $R^2$ independently are (a) hydrogen; or
(b) $C_{1-6}$alkyl.

3. The compound of claim 1 wherein $R^1$ is $CH_3$ and $R^2$ is H.

4. A pharmaceutical composition for treating topical inflammation comprising a pharmaceutical carrier and an effective amount of a compound of formula (I):

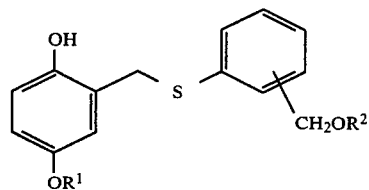

or a pharmaceutically acceptable salt thereof wherein $R^1$ and $R^2$ independently are (a) hydrogen;
(b) $C_{1-6}$alkyl;
(c) $C_{1-6}$alkenyl;
(d) $C_{1-6}$ alkanoyl;
(e) halo$C_{1-6}$alkyl;
(f) hydroxy$C_{1-6}$alkyl; or
(g) halo $C_{1-6}$alkanoyl;
(h) $C_{1-6}$cycloalkyl; and
(i) benzyl.

5. The pharmaceutical composition of claim 4 wherein: $R^1$ and $R^2$ independently are (a) hydrogen; or
(b) $C_{1-6}$ alkyl.

6. The pharmaceutical composition of claim 4 wherein $R^1$ is $CH_3$ and $R^2$ is H.

7. A method of treating or decreasing topical inflammation comprising the administration to a mammalian species in need of such treatment a therapeutically effective amount of a compound of formula I:

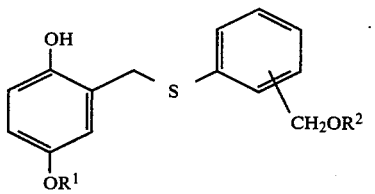

or a pharmaceutically acceptable salt thereof wherein $R^1$ and $R^2$ independently are (a) hydrogen;
(b) $C_{1-6}$alkyl;
(c) $C_{1-6}$alkenyl;
(d) $C_{1-6}$ alkanoyl;
(e) halo$C_{1-6}$alkyl;
(f) hydroxy$C_{1-6}$alkyl; or
(g) halo $C_{1-6}$alkanoyl;
(h) $C_{1-6}$cycloalkyl; and
(i) benzyl.

8. The method of claim 7 wherein: $R^1$ and $R^2$ independently are (a) hydrogen; or
(b) $C_{1-6}$ alkyl.

9. The method of claim 7 wherein $R^1$ is $CH_3$ and $R^2$ is H.

* * * * *